(12) United States Patent
Mankos et al.

(10) Patent No.: US 6,930,309 B1
(45) Date of Patent: Aug. 16, 2005

(54) DUAL-ENERGY ELECTRON FLOODING FOR NEUTRALIZATION OF CHARGED SUBSTRATE

(75) Inventors: Marian Mankos, Palo Alto, CA (US); Donald J. Parker, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/809,980

(22) Filed: Mar. 26, 2004

(51) Int. Cl.[7] ........................ H01J 37/26; G01N 23/225
(52) U.S. Cl. ........................ 250/310; 250/307; 250/309
(58) Field of Search ................................ 250/306, 307, 250/309, 310, 492.2, 492.3

(56) References Cited

U.S. PATENT DOCUMENTS

| | | |
|---|---|---|
| 4,818,872 A | 4/1989 | Parker et al. |
| 5,444,242 A | 8/1995 | Larson et al. |
| 5,576,538 A | 11/1996 | Sakai et al. |
| 5,668,368 A | 9/1997 | Sakai et al. |
| 5,959,305 A | 9/1999 | Mack et al. |
| 5,977,549 A | 11/1999 | Wang et al. |
| 6,462,332 B1 | 10/2002 | Trompenaars et al. |
| 6,570,154 B1 * | 5/2003 | Masnaghetti et al. ....... 250/310 |
| 6,600,163 B2 | 7/2003 | Halling |
| 6,610,980 B2 | 8/2003 | Veneklasen et al. |
| 6,803,571 B1 * | 10/2004 | Mankos et al. ............. 250/310 |

* cited by examiner

*Primary Examiner*—Jack I. Berman
(74) *Attorney, Agent, or Firm*—Okamoto & Benedicto LLP

(57) ABSTRACT

One embodiment disclosed relates to a method of electron beam inspection or review of a substrate having insulating materials therein. An area of the substrate is simultaneously exposed to a lower-energy electron beam and an overlapping higher-energy electron beam. The area is subsequently inspected with another electron beam. Another embodiment disclosed relates to an electron beam tool for examination of a substrate having insulating materials therein. A first cathode is configured as an electron source for a lower-energy electron beam, and a second cathode is configured as an electron source for a higher-energy electron beam. At least one electron lens is configured to focus the lower-energy electron beam and the higher-energy electron beam onto an overlapping area of a substrate. An electron beam column is subsequently used to examine the substrate.

27 Claims, 3 Drawing Sheets

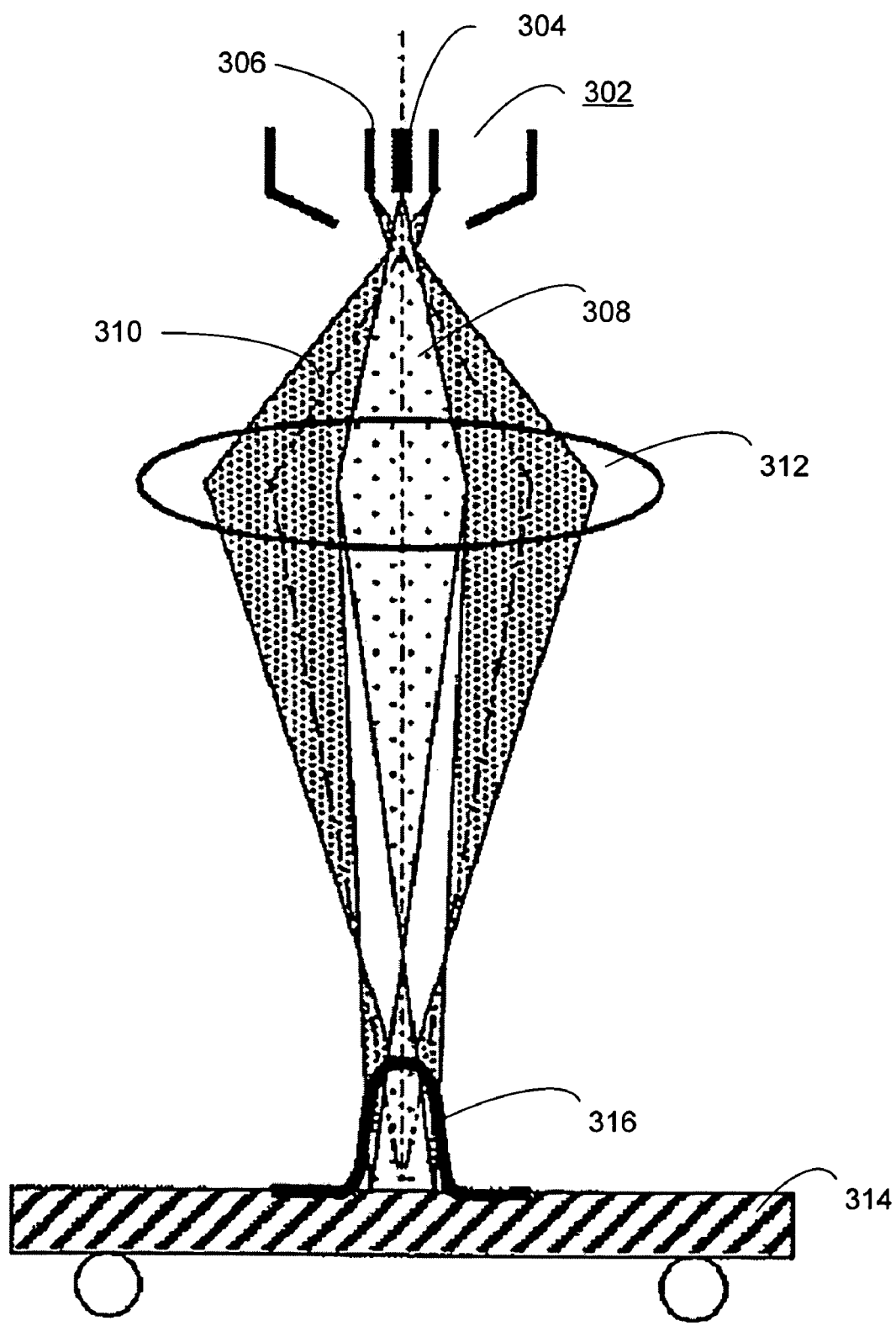
FIG. 3     300

DUAL-ENERGY ELECTRON FLOODING FOR NEUTRALIZATION OF CHARGED SUBSTRATE

BACKGROUND OF THE INVENTION

1. Field of the Invention

The present invention relates generally to specimen inspection and review. More particularly, the present invention relates to electron beam inspection and review systems.

2. Description of the Background Art

Automated inspection and review systems are important in process control and yield management for the semiconductor and related microelectronics industries. Such systems include optical and electron beam (e-beam) based systems.

In the manufacture of semiconductor devices, detection of physical defects and electrical failure earlier in the fabrication process is becoming increasingly important to shorten product development cycles and increase product yield and productivity. Advanced wafer inspection systems based on scanning electron microscopy technology have been used to detect defects and electrical failure as voltage contrast defects. However, as device design rules further shrink, and new processes (such as, for example, high aspect ratio (HAR) contacts in front-end-of-line (FEOL), HAR vias in back-end-of-line (BEOL), and dual damascene copper processes) are being widely implemented, it becomes more challenging to detect defects in device structures with smaller design rules and higher aspect ratios. Further, image contrast variation caused by uneven charge distribution can make e-beam inspection unstable or un-inspectable. Such contrast variation can occur from inside a die, from die to die, row to row, or wafer to wafer. In order to successfully inspect a wafer, control of surface charge is advantageous to 1) detect defects effectively, and 2) reduce image contrast variation during inspection.

In a conventional scanning electron microscope, a beam of electrons is scanned over a sample (e.g., a semiconductor wafer). Multiple raster scans are typically performed over an area of the sample. The beam of electrons either interact with the sample and cause an emission of secondary electrons or bounce off the sample as backscattered electrons. The secondary electrons and/or backscattered electrons are then detected by a detector that is coupled with a computer system. The computer system generates an image that is stored and/or displayed on the computer system.

Typically a certain amount of charge is required to provide a satisfactory image. This quantity of charge helps bring out the contrast features of the sample. Although conventional electron microscopy systems and techniques typically produce images having an adequate level of quality under some conditions, they produce poor quality images of the sample for some applications. For example, on a sample made of a substantially insulative material (e.g., silicon dioxide), performing one or more scans over a small area causes the sample to accumulate excess positive or negative charge in the small area relative to the rest of the sample. The excess of positive charge generates a potential barrier for some of the secondary electrons, and this potential barrier inhibits some of the secondary electrons from reaching the detector. Since this excess positive charge is likely to cause a significantly smaller amount of secondary electrons to reach the detector, an image of the small area is likely to appear dark, thus obscuring image features within that small area. Alternatively, excess negative charge build up on the sample can increase the collection of secondary electrons causing the image to saturate. In some cases, a small amount of charging is desirable since it can enhance certain image features (by way of voltage contrast) as long as it does not cause image saturation.

The excess charge remaining from a previous viewing or processing may therefore cause distortion. One solution used in SEM devices is to flood the sample with charged particles from a separate flood gun at a time separate from the inspection. This flooding equalizes the charge appearing across the sample, thus improving contrast uniformity of the images.

In regards to the focus of an electron image, a change in the surface charge for the area being imaged can also cause the image to go out of focus. Existing techniques to deal with these variations in surface charge include measuring surface charge with a Kelvin probe or secondary electron cut-off points. The data from these measurements may then be used to determine an adjustment of the focus. However, these existing techniques are disadvantageously complicated and/or inefficient. For example, measurement of surface charge with a Kelvin probe involves a large area to make the measurement and is typically slow.

Hence, as discussed above, efficient and effective control over the charge on the surface of a sample is desirable to improve the speed of obtaining images and the quality of images obtained during electron beam inspection or review. Furthermore, it is desirable to improve techniques for focusing an electron image in dependence on surface charge.

BRIEF DESCRIPTION OF THE DRAWINGS

FIG. 3 is a schematic diagram of dual-energy electron flooding with a dual-beam flood gun in accordance with an embodiment of the invention.

SUMMARY

One embodiment of the invention relates to a method of electron beam inspection or review of a substrate having insulating materials therein. An area of the substrate is simultaneously exposed to a lower-energy electron beam and an overlapping higher-energy electron beam. The area is subsequently inspected with another electron beam.

Another embodiment of the invention relates to an electron beam tool for examination of a substrate having insulating materials therein. A first cathode is configured as an electron source for a lower-energy electron beam, and a second cathode is configured as an electron source for a higher-energy electron beam. At least one electron lens is configured to focus the lower-energy electron beam and the higher-energy electron beam onto an overlapping area of a substrate. An electron beam column is subsequently used to examine the substrate.

DETAILED DESCRIPTION

Figure 1:
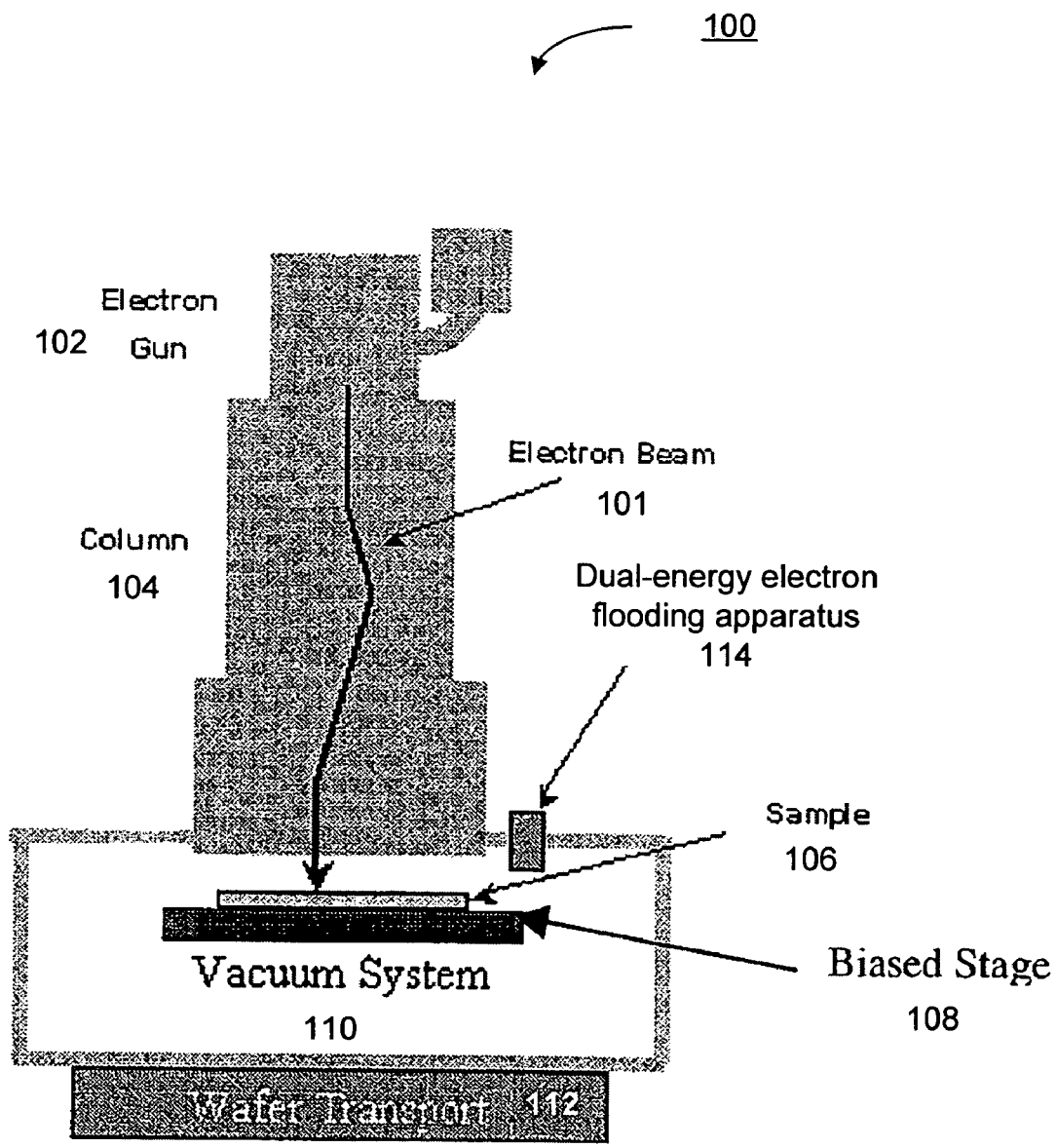
FIG. 1 is a schematic diagram of an electron beam inspection system in accordance with an embodiment of the invention.

FIG. 1 is a schematic diagram of an electron beam inspection system 100 in accordance with an embodiment of the invention. The e-beam system 100 generates and directs an incident electron beam 101 towards an area of interest on a sample or specimen 106 for use in generating an image of the area.

As shown in FIG. 1, the incident beam 101 may be generated by an electron gun 102. A column 104 including various components in a vacuum is used to direct the electron beam 101 towards the surface of the sample 106. The column 104 typically includes various electron lenses, apertures, and other components.

The sample 106 may be held on a stage 108. The stage 106 may be biased at a controllable electrical potential. Like the column 104, because the incident beam comprises electrons, a vacuum system 110 is used to pump the chamber containing the sample 106 and stage 108 (as well as the column 104). The sample 106 may comprise, for example, a wafer or other substrate. A wafer transport system 112 may be used to move wafer samples to be inspected in-line as part of a manufacturing process.

The e-beam system 100 also includes a detector (not shown) to detect charged particles (secondary electrons and/or backscattered electrons) emitted from the sample. The e-beam system 100 may also include an image generator (not shown) for forming an image from the detected emitted particles.

Some conventional e-beam systems include a single electron flood gun to flood a substrate with a broad electron beam. However, this conventional technique is disadvantageous because a single-energy beam flood gun does a poor job of discharging a substrate with insulating materials on the surface. A substantial charge typically remains with the insulating materials. The remaining charge depends on the electron beam energy used for flooding, and the secondary electron yield of the insulating material on the substrate surface. The surface, or a part of the surface, attains a non-zero electrical potential that may be rather substantial (for example, tens of volts or more).

In accordance with an embodiment of the invention, a dual-energy electron flooding apparatus 114 is included in the e-beam system 100. The dual-energy electron flooding uses two overlapping electron beams at different energies to better eliminate the charge on the substrate surface. Embodiments of the dual-energy electron flooding apparatus are discussed further below in reference to FIGS. 2 and 3.

Figure 2:
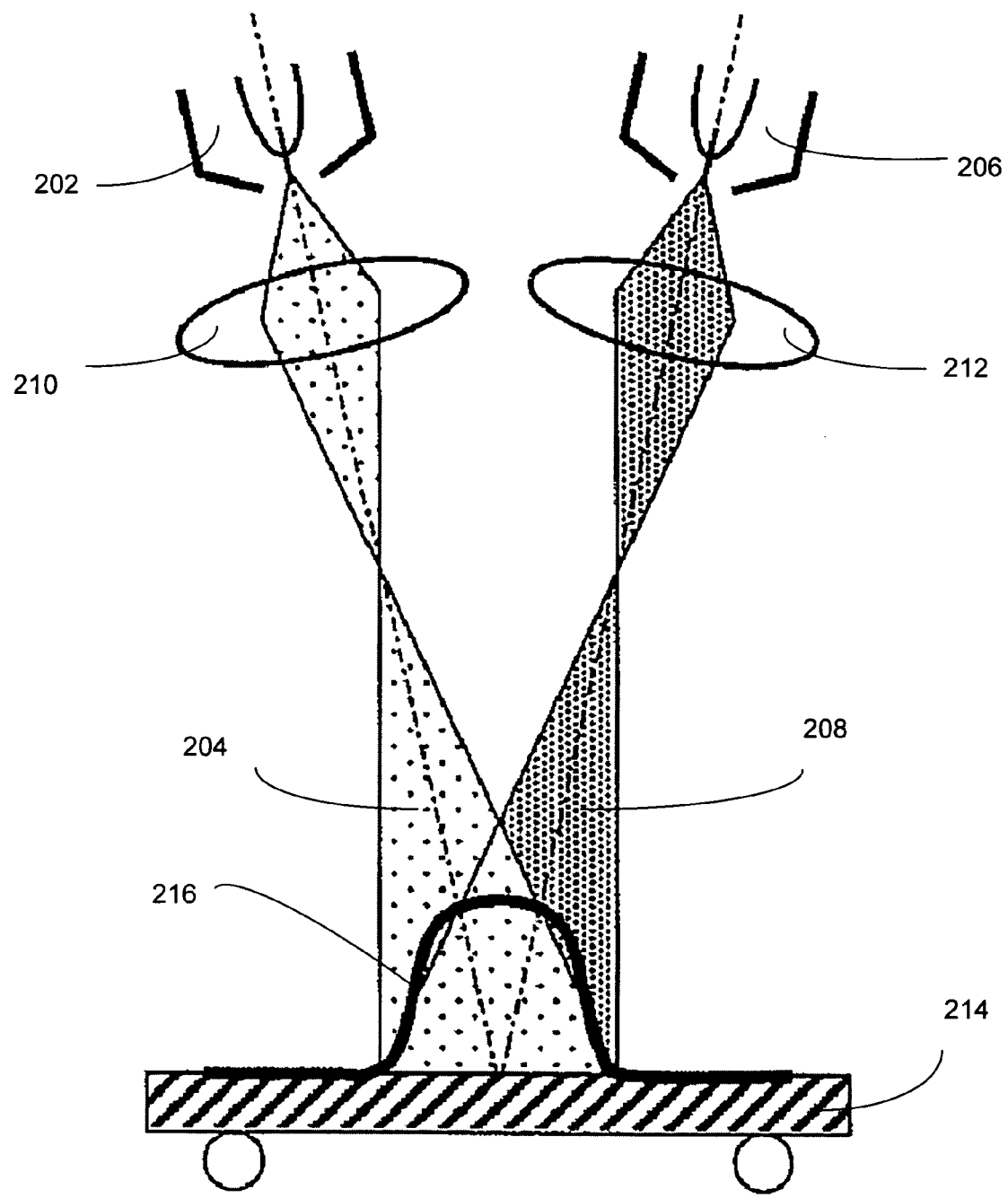
FIG. 2 is a schematic diagram of dual-energy electron flooding with two flood guns in accordance with an embodiment of the invention.

FIG. 2 is a schematic diagram of dual-energy electron flooding apparatus 200 with two independent flood guns 202 and 206 in accordance with an embodiment of the invention. The two flood guns 302 and 206 may be configured to be inclined at an angle to each other, as illustrated in FIG. 2.

A first flood gun 202 with a first cathode is configured to provide a lower-energy electron beam component 204. A second flood gun 206 with a second cathode is configured to provide a higher-energy electron beam component 208. A first electron lens system 210 focuses the lower-energy electron beam component 204 onto an area of the substrate 214. A second electron lens system 212 focuses the higher-energy electron beam component 208 onto a substantially overlapping area of the substrate 214. The substrate 214 comprises an insulating substrate or a substrate with insulating materials. A profile 216 showing an example intensity distribution across the impinged area from the two overlapping beam components is shown in FIG. 2.

FIG. 3 is a schematic diagram of dual-energy electron flooding apparatus 300 with a dual-beam flood gun 302 in accordance with an embodiment of the invention. The dual-beam flood gun 302 is configured with two cathodes 304 and 306 in the same extraction region, as illustrated in FIG. 3.

An inner cathode 304 may be configured to provide an inner electron beam component 308. An outer cathode 306 may be configured to provide an outer electron beam component 310. The inner electron beam component 308 may comprise a lower-energy beam component, and the outer electron beam component 310 may comprise a higher-energy beam component. In an alternative embodiment, the inner electron beam component 308 may comprise a higher-energy beam component, and the outer electron beam component 310 may comprise a lower-energy beam component.

An electron lens system 312 is configured to focus the inner beam component 308 onto an area of the substrate 314 and to focus the outer beam component 310 onto a substantially overlapping area of the substrate 314. A profile 316 showing an example intensity distribution across the area from the two overlapping beam components is shown in FIG. 3.

In accordance with an embodiment of the invention, the cathode source for the lower-energy beam component is biased to be at a voltage only slightly more negative than the voltage potential at the surface of the substrate. As such, the landing energy of the electrons of the lower-energy beam component is preferably low, such as, for example, less than one electron volt, or less than a few electron volts. On the other hand, the cathode source for the higher-energy beam component is biased at a more negative voltage than the cathode source for the lower-energy beam component. As such, the landing energy of the electrons of the higher-energy beam component is higher, such as, for example, on the order of a few hundred electron volts.

Impingement of each of the two e-beam components onto the area of the substrate generates a scattered beam (not illustrated). The scattered beam primarily includes (a) reflected electrons from the lower-energy beam component and (b) secondary and backscattered electrons generated by the higher-energy beam component.

The two beam components, in effect, counter-balance each other such that a dynamic equilibrium in surface charge is obtained. The lower-energy beam component serves to charge the surface negatively due to absorption by the surface of a portion of its electrons (the other portion being reflected from the surface). In other words, the yield of the lower-energy beam is less than one. The higher-energy beam component serves to charge the surface positively due to emission of scattered (secondary and/or backscattered) electrons with a yield greater than one. A yield greater than one indicates that more electrons are removed from the substrate than are absorbed by the substrate, while a yield less than one indicates that more electrons are absorbed by the substrate than are removed therefrom. In accordance with one embodiment of the invention, the result of the charging effects of the two beam components is that the surface potential of an insulating substrate becomes approximately locked to the potential of the lower-energy beam, i.e. near zero volts.

In one embodiment, the whole substrate surface is covered by scanning the overlapping beams together in a pattern (for example, a raster pattern) over the substrate. In another embodiment, if the beam size is large enough at the surface, a single exposure of the substrate to the overlapping beams may be utilized. In either case, the simultaneous, dual-energy electron beam flooding removes charge from the surface of a substrate with insulating materials, and advantageously sets the surface potential to near zero volts. The simultaneous dual-energy electron flooding may be advantageously used to reduce charging effects before an inspection or review tool is subsequently used to examine the surface of the substrate. The tool may comprise an electron beam based tool, or it may comprise a focused ion beam (FIB) tool.

The above-described diagrams are not necessarily to scale and are intended be illustrative and not limiting to a particular implementation. The above-described invention may be used in an automatic inspection or review system and applied to the inspection or review of wafers, optical masks, X-ray masks, electron-beam-proximity masks and stencil masks and similar substrates in a production environment.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of inspection or review of a substrate having insulating materials therein, the method comprising:
   simultaneously exposing an area of the substrate with a lower-energy electron beam and an overlapping higher-energy electron beam; and
   subsequently inspecting the area with another beam.

2. The method of claim 1, wherein the simultaneous exposure of the area to the lower-energy and higher-energy electron beams causes surface charge neutralization.

3. The method of claim 1, wherein the lower-energy electron beam has a landing energy of less than one electron volt.

4. The method of claim 3, wherein the higher-energy electron beam has a landing energy on the order of a few hundred electron volts.

5. The method of claim 1, further comprising:
   generating a scattered electron beam including reflected electrons from the lower-energy beam and scattered electrons caused by the higher-energy beam.

6. The method of claim 1, wherein the lower-energy electron beam is generated using a first cathode at a voltage slightly more negative than a surface voltage of the substrate.

7. The method of claim 6, wherein the higher-energy electron beam is generated using a second cathode at a voltage substantially more negative than the surface voltage of the substrate.

8. The method of claim 7, wherein the first cathode is part of a first electron gun, wherein the second cathode is part of a second electron gun, and the first and second electron guns are inclined at an angle to each other.

9. The method of claim 7, wherein the first and second cathodes are part of a dual-beam flood gun.

10. The method of claim 1, wherein the substrate comprises a semiconductor substrate for integrated circuit manufacture.

11. The method of claim 1, wherein charge neutralization of the substrate is performed by scanning the lower-energy beam and overlapping higher-energy beam over the substrate.

12. The method of claim 1, wherein charge neutralization of the substrate is performed by a single exposure of the lower-energy beam and overlapping higher-energy beam.

13. An electron beam tool for examination of a substrate having insulating materials therein, the electron beam tool comprising:
   a first cathode configured as an electron source for a lower-energy electron beam;
   a second cathode configured as an electron source for a higher-energy electron beam;
   at least one electron lens configured to focus the lower-energy electron beam and the higher-energy electron beam onto an overlapping area of a substrate; and
   an electron beam column for subsequent examination of the substrate.

14. The electron beam tool of claim 13, wherein the simultaneous exposure of the area to the lower-energy and higher-energy electron beams causes surface charge neutralization.

15. The electron beam tool of claim 13, wherein the lower-energy electron beam has a landing energy of less than one electron volt.

16. The electron beam tool of claim 15, wherein the higher-energy electron beam has a landing energy on the order of a few hundred electron volts.

17. The electron beam tool of claim 13, wherein a scattered electron beam is generated that includes reflected electrons from the lower-energy beam and scattered electrons caused by the higher-energy beam.

18. The electron beam tool of claim 13, wherein the first cathode is controlled to be at a voltage slightly more negative than a surface voltage of the substrate.

19. The electron beam tool of claim 18, wherein the second cathode is controlled to be at a voltage substantially more negative than the surface voltage of the substrate.

20. The electron beam tool of claim 19, wherein the first cathode is part of a first electron gun, wherein the second cathode is part of a second electron gun, and the first and second electron guns are inclined at an angle to each other.

21. The electron beam tool of claim 19, wherein the first and second cathodes are part of a dual-beam flood gun.

22. The electron beam tool of claim 13, wherein the substrate comprises a semiconductor substrate for integrated circuit manufacture.

23. The electron beam tool of claim 13, wherein charge neutralization of the substrate is performed by scanning the lower-energy beam and overlapping higher-energy beam over the substrate.

24. The electron beam tool of claim 13, wherein charge neutralization of the substrate is performed by a single exposure of the lower-energy beam and overlapping higher-energy beam.

25. An apparatus for inspection or review of a substrate having insulating materials therein, the apparatus comprising:
   means for simultaneously exposing an area of the substrate with a lower-energy electron beam and an overlapping higher-energy electron beam; and
   means for subsequently inspecting the area with another beam.

26. The apparatus of claim 25, wherein the other beam comprises an electron beam.

27. The apparatus of claim 25, wherein the other beam comprises a focused ion beam.

* * * * *